United States Patent
Köhler

(10) Patent No.: US 11,648,358 B2
(45) Date of Patent: May 16, 2023

(54) AEROSOL GENERATOR WITH OFFSET INLET

(71) Applicant: NLI GMBH, Marburg (DE)

(72) Inventor: Niklas Köhler, Wuppertal (DE)

(73) Assignee: NLI GmbH, Marburg (DE)

( * ) Notice: Subject to any disclaimer, the term of this patent is extended or adjusted under 35 U.S.C. 154(b) by 0 days.

(21) Appl. No.: 16/968,544

(22) PCT Filed: Feb. 8, 2019

(86) PCT No.: PCT/EP2019/053109
§ 371 (c)(1),
(2) Date: Aug. 20, 2021

(87) PCT Pub. No.: WO2019/157975
PCT Pub. Date: Aug. 15, 2019

(65) Prior Publication Data
US 2021/0369984 A1    Dec. 2, 2021

(51) Int. Cl.
*A61M 11/00* (2006.01)
*A61M 15/00* (2006.01)

(52) U.S. Cl.
CPC ......... *A61M 11/002* (2014.02); *A61M 11/005* (2013.01); *A61M 15/0085* (2013.01); *A61M 2206/16* (2013.01)

(58) Field of Classification Search
CPC .............. A61M 11/002; A61M 15/001; A61M 15/0085; A61M 11/005; B05B 17/0615
See application file for complete search history.

(56) References Cited

U.S. PATENT DOCUMENTS

| | | | | |
|---|---|---|---|---|
| 3,804,280 | A | * | 4/1974 | van Amerongen ...... B65D 1/06 215/384 |
| 3,806,100 | A | * | 4/1974 | Cornett, III ....... A61M 15/0085 261/1 |
| 3,828,773 | A | * | 8/1974 | Buch .................. A61M 15/0085 128/200.16 |

(Continued)

FOREIGN PATENT DOCUMENTS

| | | | |
|---|---|---|---|
| DE | 10102526 A1 | 7/2002 | |
| DE | 10102526 B4 * | 10/2007 | ............ A61M 16/00 |

(Continued)

*Primary Examiner* — Kathryn E Ditmer
(74) *Attorney, Agent, or Firm* — Weitzman Law Offices, LLC

(57) ABSTRACT

An aerosol generator with an active liquid container and a nebulization chamber associated therewith, which is connected to an inlet channel for the supply of carrier gas and to an outlet channel for the discharge of carrier gas mixed with aerosol obtained from the active liquid, is intended to enable a particularly good adjustability of the droplet size of the aerosols contained in the discharged carrier gas and thus a use particularly in the context of a transnasal inhalation therapy. For this purpose, the nebulization chamber has a substantially rotationally symmetrical boundary wall, the inlet channel being positioned and oriented in the region of its point of entry into the nebulization chamber in such a way that its longitudinal axis is offset relative to the axis of symmetry of the nebulization chamber in the region of the point of entry and does not intersect the axis of symmetry.

5 Claims, 2 Drawing Sheets

(56) References Cited

U.S. PATENT DOCUMENTS

| | | | | |
|---|---|---|---|---|
| 3,892,235 A | * | 7/1975 | Van Amerongen | B65D 1/06 |
| | | | | 128/200.16 |
| 5,596,982 A | | 1/1997 | Blaha-Schnabel | |
| 6,127,429 A | * | 10/2000 | Katusic | B01F 3/0407 |
| | | | | 118/303 |
| 7,834,225 B1 | * | 11/2010 | Adiga | B05B 7/0012 |
| | | | | 568/913 |
| 2007/0035044 A1 | * | 2/2007 | Chiu | F24F 6/02 |
| | | | | 261/81 |
| 2008/0074864 A1 | * | 3/2008 | Molders | F24F 6/12 |
| | | | | 362/101 |
| 2012/0174916 A1 | | 7/2012 | Kern | |
| 2016/0256637 A1 | | 9/2016 | Kern | |
| 2017/0157280 A1 | * | 6/2017 | Young | A61L 9/14 |

FOREIGN PATENT DOCUMENTS

| | | | | |
|---|---|---|---|---|
| FR | 2690510 A1 | * | 10/1993 | B05B 17/0615 |
| JP | 55124566 A | * | 9/1980 | B05B 17/0615 |
| WO | 9301891 A1 | | 2/1993 | |
| WO | WO-0015282 A1 | * | 3/2000 | A61M 11/002 |
| WO | 2010149144 A1 | | 12/2010 | |
| WO | 2012079684 A1 | | 6/2012 | |

* cited by examiner

AEROSOL GENERATOR WITH OFFSET INLET

CROSS REFERENCE TO RELATED APPLICATIONS

This application is the national phase of PCT/EP2019/053109, filed Feb. 8, 2019, which is hereby incorporated by reference in full. PCT/EP2019/053109 itself derives priority from EP 18155701.8, filed Feb. 8, 2018.

FIELD OF INVENTION

The invention relates to an aerosol generator with a container for an active liquid and a nebulization chamber associated therewith, which is connected to an inlet channel for the supply of carrier gas and to an outlet channel for the discharge of carrier gas mixed with aerosol obtained from the active liquid.

BACKGROUND

Aerosol generators of this type can be used, for example, in so-called inhalers to nebulize an active ingredient or a drug in the form of a liquid or to produce fine and ultra-fine droplets from it. In the form of an aerosol produced in this way, the active substance or drug can then be mixed with a patient's breath and introduced into the respiratory tract via the air inhaled. Such an administration of active substances or drugs into the respiratory tract via the respiratory air can be very effective and efficient, since a rapid and low-loss transfer into the bloodstream can take place from the lungs.

Also, it is known from WO 2012/079684 A1 that active substance aerosols generated by such an aerosol generator can be administered as part of a transnasal inhalation therapy, whereby, if carried out appropriately, i.e. in particular if administered comparatively slowly with a particularly small droplet size, the active substance can be deposited comparatively deep in the lung and thus efficiently at the desired site of action, namely in the lung periphery. For such applications in particular, it is desirable to be able to adjust and control the droplet size of the droplets produced in the aerosol generator with particular precision.

From WO 2010/149144 A1 an aerosol generator of the abovementioned type is known, which should enable a reliable generation of aerosol droplets with a small droplet size while keeping the flow resistance for breathing low. For this purpose, the known aerosol generator comprises a nebulization chamber which is essentially cylindrical in shape. The carrier gas flowing into this chamber, i.e. in particular the breathing air for the patient, is set in a swirl around the cylinder axis by means of a guide vane arrangement in the nebulization chamber, in which the aerosol obtained from the active fluid is also "loaded". Centrifugal force causes the comparatively large and correspondingly heavy aerosol droplets to be pressed against the inside of these guide vanes, where they are agglomerated and separated into droplets, so that they are returned along the wall of the housing into the active ingredient container. With this arrangement, the supply of undesired large aerosol droplets to the outlet channel of the aerosol generator can be limited; however, further control or even specific adjustment of a desired droplet size in the aerosol-enriched breathing air discharged on the outlet side is not possible with this system.

An aerosol generator according to the preamble of claim 1 is known from US 2012/174916 A1. Alternative designs of nebulizers are known from WO 93/01891 A1, U.S. Pat. No. 5,596,982, DE 101 02 526 A1 or US 2016/256637 A1.

SUMMARY OF THE INVENTION

It is therefore an object of the present invention to provide an aerosol generator of the type mentioned above with which the droplet size of the aerosols contained in the delivered carrier gas can be particularly well adjusted and which is thus particularly suitable for use in the context of a transnasal inhalation therapy.

According to the invention, this object is achieved by the nebulization chamber having a substantially rotationally symmetrical boundary wall, the inlet channel being positioned and oriented in the region of its point of entry into the nebulization chamber in such a way that its longitudinal axis is offset relative to the axis of rotation of the nebulization chamber in the region of the point of entry and does not intersect the axis of rotation, the inlet channel entering the nebulization chamber through the boundary wall.

Advantageous features of the invention are the subject of the dependent claims.

The invention is based upon the consideration that by using a rotation or swirl of the aerosol-laden carrier gas flowing through the nebulization chamber for the separation of undesirably large aerosol droplets at the boundary wall, the adjustability of the droplet size can be further improved by providing an additional degree of freedom to influence the centrifugal separation. In order to make this possible, it is planned to generate the swirl or rotation of the carrier gas flowing through the nebulization chamber independently of static installations within the nebulization chamber. This can be achieved in a particularly simple manner by designing the aerosol generator for an off-center feed of the carrier gas into the nebulization chamber, i.e. offset to the axis of rotation or symmetry of the nebulization chamber. The carrier gas should thus be fed into the nebulization chamber in an inflow direction which has a tangential component with respect to its axis of rotation when entering the nebulization chamber. The swirl and thus the angular velocity of the carrier gas rotation within the nebulization chamber can be influenced by adjusting or controlling the carrier gas parameters during the inflow, e.g. volume flow and/or velocity. In particular, the gas and/or aerosol can thus be set in rotation in a controlled manner In a preferred embodiment, the inlet channel of the nebulization chamber is connected to a pump unit, especially a fan or "blower". The pump unit can be adjusted in terms of its delivery rate, so that the inflow rate and/or velocity of the carrier gas flowing into the nebulization chamber can be adjusted, thus allowing the aerosol size, i.e. the average size of the aerosol droplets, to be regulated.

The nebulization of the active liquid can be carried out with any nebulizer of suitable design, for example a nozzle nebulizer. Preferably, an ultrasonic nebulizer is provided for this purpose. The ultrasonic nebulizer preferably comprises a piezoelectric crystal in a design known per se, which generates ultrasound, whereby the ultrasound is transmitted to the active fluid in the active fluid container and forms a bubble on its surface, from which fine droplets are separated as an aerosol.

When the active liquid is atomized, in particular by means of ultrasound, a column of liquid can be formed above the liquid level, in particular in the forming bubble. In order to limit the height of the liquid column by simple means and to ensure the separation of particularly large liquid droplets in a particularly simple manner, in a preferred embodiment a baffle plate is arranged in the nebulization chamber opposite the active liquid container. The largest liquid droplets in particular are deposited on the baffle plate so that they can drip back into the active liquid tank from the baffle plate. The distance between the baffle plate and the active liquid tank or the surface of the active liquid can be adjusted in an advantageous embodiment so that the height of the liquid column and the droplet separation can be influenced in a particularly simple way depending on the requirements and operating mode. In particular, the combination of adjustable distance between the baffle plate and the active fluid, which is considered to be particularly advantageous and independently inventive, on the one hand, and the adjustable feed rate of the carrier gas into the nebulization chamber, on the other hand, can have a particularly effective influence on the particle size of the aerosol produced.

In a preferred embodiment, this is achieved in a particularly simple way by placing the baffle plate in front of the inlet opening of the outlet duct and at a distance from it.

A particularly simple and thus cost-effective preferred design can be achieved in which the outlet channel is advantageously formed by an outlet pipe which is guided in its longitudinal direction by a cover flange of the nebulization chamber. In particular, the outlet pipe can be screwed into the cover flange with a thread, so that a twisting of the outlet pipe in the cover flange is converted into a displacement in the longitudinal direction via the thread. The baffle plate is preferably attached to the end of the outlet tube at a distance from the inlet opening of the outlet tube, for example by means of webs, so that the height of the positioning of the baffle plate above the active fluid can be changed by moving the outlet tube in the cover flange, for example by twisting it. Such a height adjustment, for example by twisting, can be done manually. However, increased precision can be achieved in such a system by providing automated height adjustment, e.g. by means of a stepper motor, as part of another advantageous embodiment. This can act directly on the linear positioning of the baffle plate mounted on the outlet tube or it can also cause the outlet tube to be rotated and thus effect the height adjustment via the thread.

It is advantageous that the outlet channel, at least in the region where it merges into the nebulization chamber, is aligned with its longitudinal direction substantially parallel to the cylinder or symmetry axis of the nebulization chamber, so that the carrier gas loaded with the aerosol flows out of the nebulization chamber in a direction substantially parallel to the axis of rotation of the nebulization chamber. With respect to the cylinder coordinate system of the nebulization chamber, the carrier gas thus flows out essentially in an axial direction and thus orthogonally to the tangential directional component of the inflowing carrier gas. This means that the desired swirl can be generated and adjusted particularly effectively via the flow conditions of the carrier gas in the nebulization chamber.

Preferably, the carrier gas is oxygen or an oxygen-containing gas, so that the carrier gas is also particularly suitable as a breathing gas for the patient or user. The oxygen-containing carrier gas can be supplied from an oxygen supply or from an oxygen concentrator from the nebulization chamber, for example. To make this possible, the nebulization chamber and/or the fan or blower connected upstream of it on the gas side is connected to an oxygen supply or an oxygen concentrator on the input side.

In a further advantageous design, the boundary wall and/or the cover of the nebulization chamber is provided with a refill opening for the active fluid, so that the aerosol generator can be refilled with active fluid, for example with a syringe, without dismantling the fogging chamber. In another particularly preferred design, the nebulization chamber is connected via the refill opening or via a suitable connecting line to an external reservoir or a reservoir for active liquid, so that the liquid level of the active liquid and thus its liquid level can be kept constant or constant by means of a suitable refill.

The advantages achieved with the invention consist in particular in the fact that a twist or a rotation of the gas in the nebulization chamber can be set particularly effectively and also changed in a simple manner by the eccentric supply of the carrier gas with respect to the axis of rotation of the atomization chamber, in particular in connection with its discharge parallel to the axis of rotation. In this way, the centrifugal forces acting on the gas in the nebulization chamber due to twist or rotation can be used specifically for size-dependent droplet separation and can be changed according to requirements and situation. This enables a targeted influence on the droplet size of the aerosol carried in the outflowing carrier gas.

BRIEF DESCRIPTION OF THE DRAWINGS

By way of example, embodiments of the present invention are explained further on the basis of the following drawings. The figs. show.

Identical parts are marked with the same reference signs in all figures.

DETAILED DESCRIPTION

Figure 2:
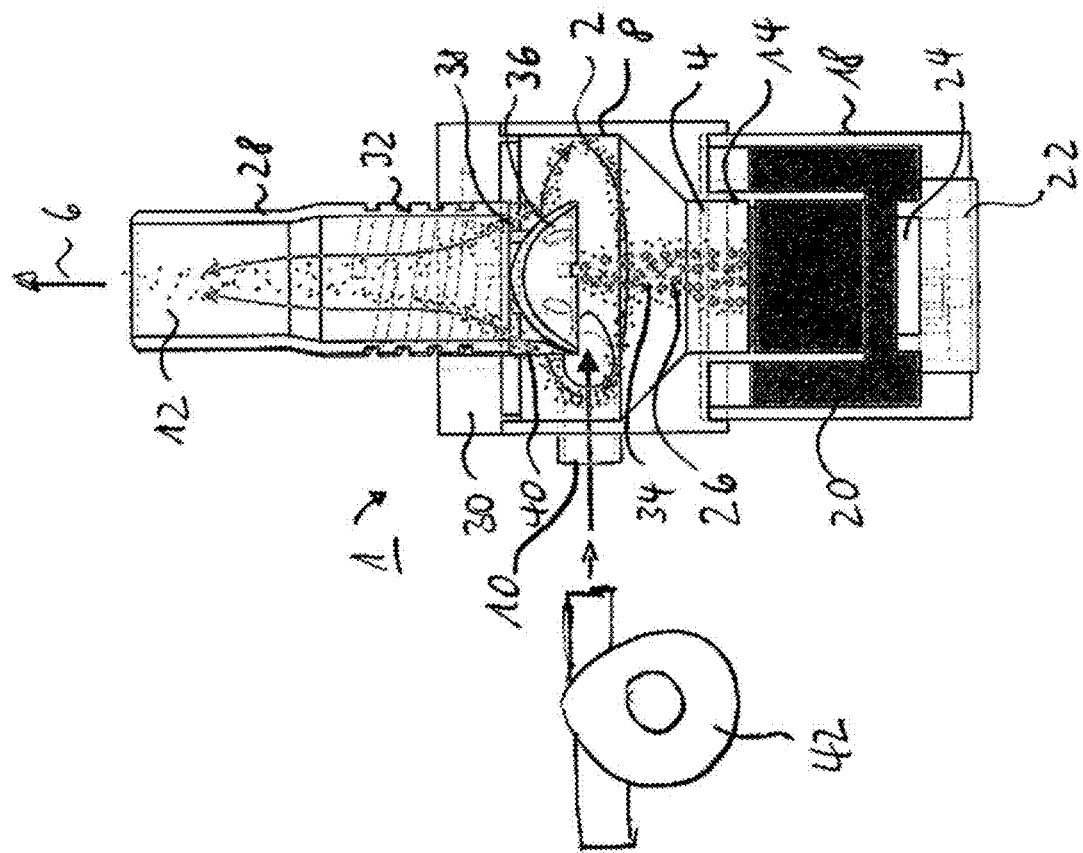
FIG. 2 the aerosol generator according to FIG. 1 in longitudinal section.

The aerosol generator 1 according to the figures is intended for generating an aerosol from an active substance or drug present in the form of a liquid, hereinafter referred to as "active substance liquid", and for loading a carrier gas with the generated aerosol or droplet mist. For this purpose, the aerosol generator 1 comprises a nebulization chamber 2 and an associated container 4 for the active substance fluid, in which the active liquid to be nebulized is stored. The nebulization chamber 2 has a substantially rotationally symmetrical design with respect to its central axis indicated by arrow 6 and is bounded in the radial direction by a substantially cylindrical boundary wall 8.

The nebulization chamber 2 is connected to an inlet channel 10 for the supply of carrier gas, for example the breathing air of a patient, and to an outlet channel 12 for the discharge of carrier gas mixed with aerosol obtained from the active liquid.

The active substance container 4, which is kept open at the top and thus connected on the gas side to the interior of the nebulization chamber 2, comprises a solid annular outer wall 14 for receiving the active substance or drug, which is connected in the bottom area to a bottom membrane 16, preferably formed from polyvinyl chloride (PVC), which forms the lower closure. To the outside and towards the bottom, the active substance container 4 is surrounded in the assembled state by a sound transmission body 18, which in turn forms an inner chamber 20 which is usually completely filled with water during operation. The PVC diaphragm 16 ensures that the medium to be nebulized does not mix with the water in the base tank and possibly comes into contact with the nebulizer diaphragm. The sound transmission body 18 is in turn mounted on an ultrasonic nebulizer 22. During operation of the aerosol generator 1, the piezo crystal 24 generates ultrasound, which is transmitted via the sound transmission body 18, and in particular via the water in the inner chamber 20, to the base membrane 16 of the active ingredient container 4 and coupled into the active ingredient via this membrane. The ultrasound is thus transmitted to the active fluid in the active fluid tank 4 and causes it to vibrate. As a result, a bubble 26 forms on the surface of the active liquid, from which fine droplets are separated as an aerosol. This multi-component version of the aerosol generator 1 makes cleaning much easier during operation.

The outlet channel 12 is formed by an outlet pipe 28, which is led through a cover flange 30 of the nebulization chamber 2. The cover flange 30 seals the misting chamber 2 at the top. In the area of the lead-through, the outlet pipe 28 is provided with an external thread 32, which interacts with a corresponding internal thread in the cover flange 30. Via this thread combination, the outlet pipe 28 is screwed into the cover flange 30, so that a twisting of the outlet pipe 28 in the cover flange 30 is converted into a longitudinal displacement. In the design example, the outlet channel 12 and, with it, the outlet tube 28 are aligned with their longitudinal direction essentially parallel to the axis of rotation or symmetry of the nebulization chamber 2 indicated by the arrow 6, so that the carrier gas loaded with the aerosol flows out of the nebulization chamber 2 in a direction essentially parallel to the axis of rotation of the nebulization chamber 2.

As can be seen in particular in the sectional view in FIG. 2, a liquid column 34 with a high droplet or liquid density is formed in the bubble 26 forming above the liquid level of the active substance liquid when the aerosol generator 1 is operated. In order to limit its height and at the same time enable the separation of particularly large liquid droplets, a baffle plate 36 is arranged in the nebulization chamber 2 opposite the active liquid container 4. The largest liquid droplets in particular are deposited on this plate so that they can drop from the baffle plate 36 back into the active liquid tank 4.

The baffle plate 36 is attached to the outlet pipe 28 at the end of the outlet pipe and at a distance from the inlet opening 38 of the outlet pipe 28 via a number of support bars 40. By moving the outlet tube 28 in the cover flange 30, e.g. by twisting it, the height of the positioning of the flapper plate 36 above the active liquid can be changed. The height of the liquid column 34 and the droplet separation at the flapper plate 36 can thus be influenced in a particularly simple manner depending on the requirements and operating mode.

The aerosol generator 1 is designed to adjust the droplet size of the aerosols contained in the delivered carrier gas so that it can be used particularly well in the context of a transnasal inhalation therapy. For this purpose, the aerosol generator 1 is designed for flow guidance of the carrier gas in the nebulization chamber 2, in which the carrier gas is guided on a spiral flow path and subjected to an impressed swirl. The design of the nebulizer or aerosol generator 1 is based on the concept of achieving the smallest possible aerosol particle size by means of particle separation using centrifugal force. A suitably supplied air flow within the cylindrical nebulizer housing is intended to cause a collision of massive aerosol particles on the inner wall of the nebulizer, depending on the flow and particle size. Thus, only comparatively small aerosol particles, which are important for the transnasal inhalation therapy, reach the outlet channel 12.

Figure 1:
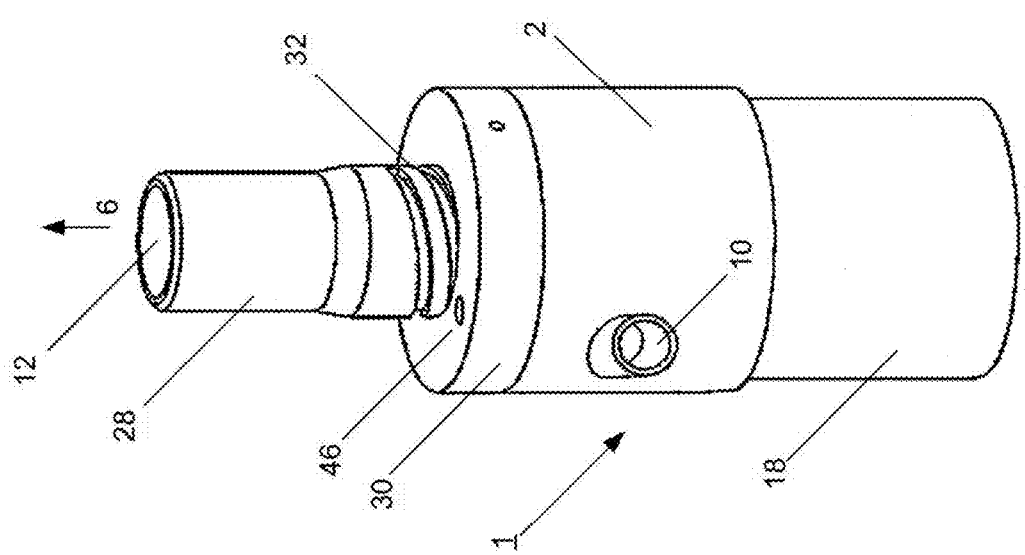
FIG. 1 an aerosol generator in perspective view.
Figure 3:
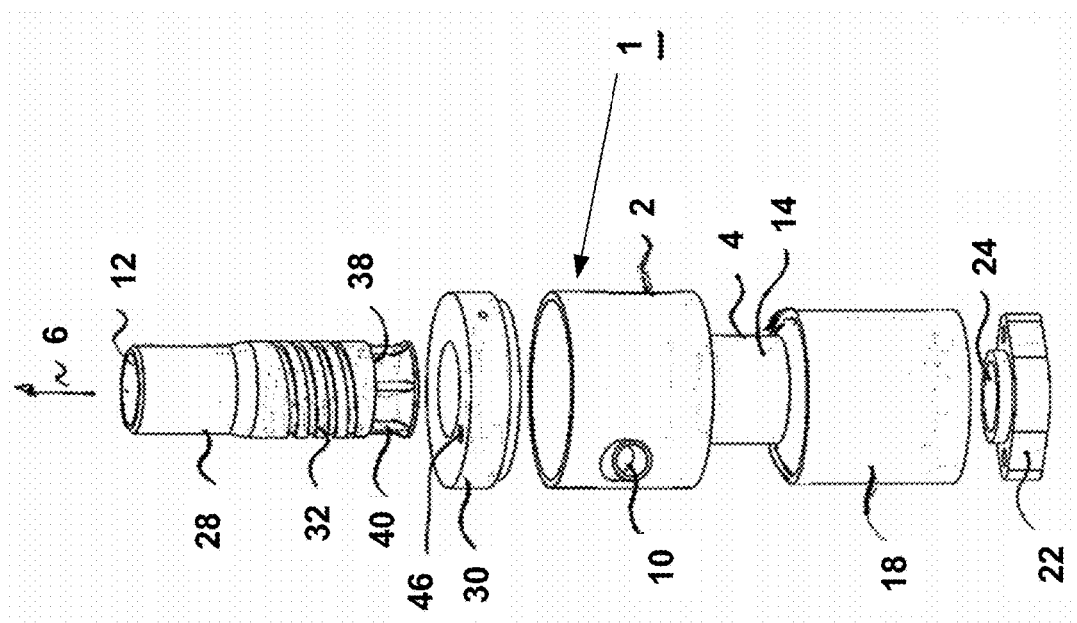
FIG. 3 the aerosol generator according to FIG. 1 in exploded view.

In order to enable the desired swirl or rotation generation in a particularly simple way, a suitable supply of carrier air into the nebulization chamber 2 is provided, namely an off-center supply on the one hand and a supply under suitably selected feed pressure on the other. For this purpose, the inlet channel 10 is positioned and oriented eccentrically in the region of its point of entry into the nebulization chamber 2 in such a way that its longitudinal axis in the region of the point of entry is offset relative to the axis of rotation of the nebulization chamber 2 indicated by the arrow 6 and does not intersect the axis of rotation. This arrangement is particularly evident in the perspective depictions in FIGS. 1 and 3. Furthermore, as can be seen in the sectional drawing in FIG. 2, the inlet channel 10 is connected on the inlet side to a pump unit 42, by means of which the inflow rate and/or speed of the carrier gas flowing into the nebulization chamber 2 can be adjusted. In the design example, a suitably selected fan or "blower" is provided as pump unit 42.

By this positioning of the inlet channel 10, possibly in combination with the adjustable feed rate of the carrier gas via the pump unit 42, the carrier gas flowing into the nebulization chamber 2 is set into the desired swirl around the axis of rotation. Centrifugal force causes the comparatively large and correspondingly heavy aerosol droplets to be pressed against the inner boundary wall 8 and separated there, so that they are returned along the housing wall and over the wall 44 of the nebulization chamber 2, which is bevelled in the lower area, into the active fluid container 4. The flow (also called volume flow), which accelerates the aerosol in the nebulization chamber 2 to a circular movement, is generated in the pump unit 42, whereby the flow generated is regulated by changing the rotational speed of the fan/blower.

The cover flange 30 of the fogging chamber 2 is provided with a refill opening 46 for the active fluid, so that, for example with a syringe, refilling of the aerosol generator 1 with active fluid is possible without dismantling the fogging chamber 2. Alternatively or additionally, the refill opening 46 can of course also be located in the boundary wall 8.

Figure 4:
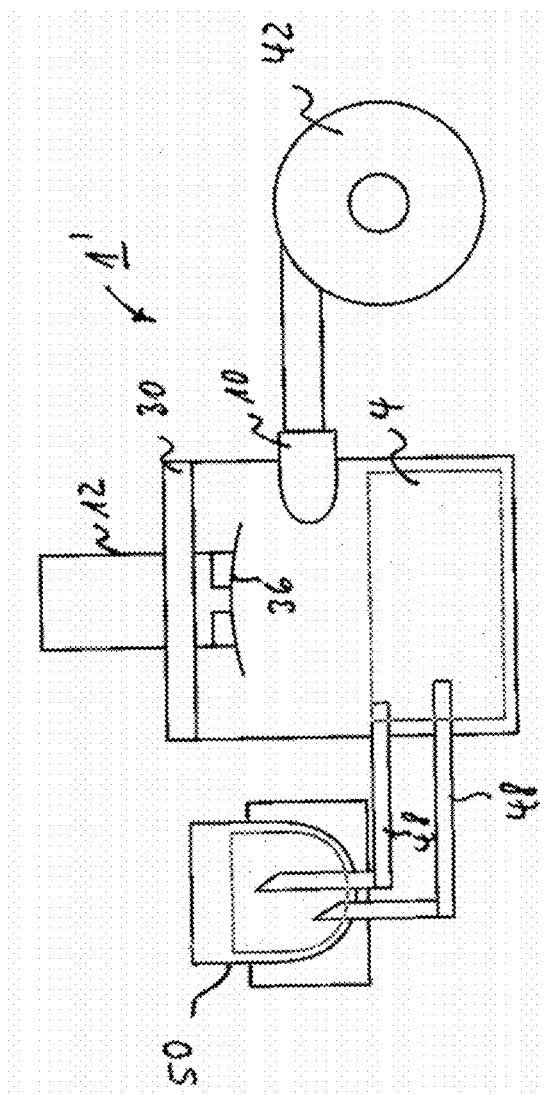
FIG. 4 schematically, in section, an alternative embodiment of an aerosol generator with an external storage tank.

In the alternative design example according to FIG. 4, the active fluid tank 4 of the aerosol generator 1' is connected to an external reservoir or storage tank 50 for active fluid via a number of media lines 48. Via this reservoir or reservoir, the active fluid can also be used during the operation of the aerosol generator 1'.

REFERENCE NUMERALS

1 Aerosol generator
2 Nebulization chamber
4 Active fluid reservoir
6 Arrow
8 Boundary wall
10 Inlet port
12 Exhaust duct
14 External wall
16 Bottom membrane
18 Sound transmitting body
20 Inner chamber
22 Ultrasonic nebulizer
24 Piezo crystal
26 Bubble
28 Outlet pipe 30 Cover flange
32 External thread
34 Fluid column
36 Baffle plate
38 Intake opening
40 Carrier bar
42 Pump unit
44 Wall
46 Refill opening
48 Media line
50 Storage tank

What is claimed:

1. An aerosol generator with a container for an active liquid, and with a nebulization chamber associated therewith, in which a bubbling of the active liquid can be generated above the liquid level of the active liquid by means of an associated ultrasonic nebulizer, wherein the nebulization chamber is connected to an inlet channel for supplying carrier gas and to an outlet channel for discharging carrier gas mixed with aerosol obtained from the active liquid and has a substantially rotationally symmetrical boundary wall, wherein the inlet channel is positioned and oriented in the region of its point of entry into the nebulization chamber in such a way that its longitudinal axis in the region of the point of entry is offset relative to an axis of symmetry of the nebulization chamber, which axis of symmetry is defined by the rotationally symmetrical boundary wall, and does not intersect the axis of symmetry, wherein the inlet channel opens through the boundary wall into the nebulization chamber at a location between the active liquid container and a baffle plate arranged opposite the active liquid container and adjustable along the longitudinal axis to vary a distance between the baffle plate and the active liquid container, wherein the baffle plate is adjustable along the longitudinal axis via rotation of a screw-threaded exhaust tube that comprises both the baffle plate and the outlet channel.

2. The aerosol generator of claim 1, the inlet channel of which is connected on an inlet side thereof to a pump unit by means of which the inflow rate or speed of the carrier gas flowing into the nebulization chamber can be adjusted.

3. The aerosol generator of claim 1, in which the baffle plate is arranged in front of an inlet opening of the outlet channel and at a distance from it.

4. The aerosol generator of claim 1, wherein the exhaust tube is guided displaceably in its longitudinal direction through a cover flange of the nebulization chamber.

5. The aerosol generator of claim 1, in which the boundary wall and/or a cover flange of the nebulization chamber has a number of refilling openings for the active liquid.

* * * * *